United States Patent [19]
Mathews et al.

[11] Patent Number: 4,743,680
[45] Date of Patent: May 10, 1988

[54] METHOD FOR PURIFYING ANTIHEMOPHILIC FACTOR

[75] Inventors: Rita W. Mathews; Alan J. Johnson, both of New York, N.Y.

[73] Assignee: New York University, New York, N.Y.

[21] Appl. No.: 697,267

[22] Filed: Feb. 1, 1985

[51] Int. Cl.⁴ ............ C07G 7/00; A61K 35/14; A61K 35/16; C07K 3/20
[52] U.S. Cl. ................ 530/383; 530/384; 530/412; 530/413; 530/415; 210/656; 210/927; 514/822; 424/101
[58] Field of Search .......... 260/112 B, 112 R; 210/656, 927; 514/2, 822; 424/101; 530/383, 384, 412, 413, 415

[56] References Cited

U.S. PATENT DOCUMENTS

| | | | |
|---|---|---|---|
| 4,348,315 | 9/1982 | Blombäck et al. | 260/112 B |
| 4,387,092 | 6/1983 | Liautaud et al. | 260/112 B |
| 4,404,131 | 9/1983 | Schwarz et al. | 260/112 B |
| 4,404,132 | 9/1983 | Mitra | 260/112 B |
| 4,439,357 | 3/1984 | Bonhard et al. | 260/112 B |
| 4,508,709 | 4/1985 | Amphlett et al. | 424/101 |

FOREIGN PATENT DOCUMENTS

A2173242  3/1986  European Pat. Off.
2635894  2/1978  Fed. Rep. of Germany
3432083  4/1985  Fed. Rep. of Germany

OTHER PUBLICATIONS

Lundblad et al, "The Effect of Dextrose on Chromatography of Antihemophilic Factor (Factor VIII), *Thrombosis Research*, 1:197, 1972, pp. 197–200.
Austen et al, "Factor VIII Fractionation on Aminohexyl Sepharose with Possible Reduction in Hepatitis B Antigen", *Thromb. Haemastas.*, 48(1): 46 (1982).
Faure et al, "Improved Buffer for the Chromatographic Separation of Factor VIII Coagulant", *J. Chromatog.*, 257:387 (1983).

*Primary Examiner*—John Kight
*Assistant Examiner*—Nathan M. Nutter
*Attorney, Agent, or Firm*—Darby & Darby

[57] ABSTRACT

Disclosed are methods for purifying proteins including AHF by column chromatography in the presence of additives including sugars and polyhydric alcohols which serve to increase the electrostatic forces on the surface of said proteins while decreasing the hydrophobicity of said proteins resulting in preparations of such proteins of high purity and/or resolution and/or recovery.

24 Claims, 3 Drawing Sheets

METHOD FOR PURIFYING ANTIHEMOPHILIC FACTOR

The U.S. Government has rights to this invention by virtue of grants No. R01 HL 29688 and No. RR 053-99 from the U.S. Department of Health and Human Services.

BACKGROUND OF THE INVENTION (a) Field of the Invention

This invention relates to a method for purifying proteins. More particularly, this invention relates to a high-recovery, high-resolution method of purifying antihemophilic factor VIIII:C ("AHF") by using column chromatography techniques in the presence of sugars, polyhydric alcohols, amino acids, or salts. The AHF preparations obtained by the present invention are also of high purity.

Factor VIII procoagulant protein (AHF) is a plasma protein that has the ability to correct the clotting defect in hemophilic plasma. In fact, the activity of AHF is measured by its ability to induce clotting in hemophilia A plasma.

One unit of AHF is the amount present in one milliliter of normal, adult male plasma. The standard used herein, a World Health Organization Standard, is available from the National Institute for Biological Standards and Control, Holly Hill, Hampstead, London NY3 6RD, England.

(b) Discussion of the Prior Art

The primary therapeutic use of AHF has been its intravenous administration to hemophilic patients. At first, this involved infusion of whole blood or fresh-frozen plasma, which required long infusion times and often caused hypervolemia.

Use of plasma cryoprecipitate ("cryo") still required long infusion times. The cryo was not completely soluble in the solvent used for infusion and required filtration. Its AHF content was low and highly variable. A large cryo volume was required, and assaying multiple sealed sterile containers for AHF content before use was very cumbersome and often omitted. Thus, the exact amount of cryo available for therapy could not be ascertained. Moreover, cryo required storage at $-20°$ C. in large plastic blood bags and, therefore, availability of large refrigeration facilities. This primitive method made at-home treatment impossible.

Use of lyophilized AHF concentrates solved many of the above problems. The concentrates are generally obtained by subjecting plasma to cryoprecipitation followed by a second precipitation with polyethylene glycol. The concentrates are stable under refrigeration; they dissolve completely in the reconstituting liquid, and may be reconstituted in lower volumes than cryo (10-30 ml) to give assayable concentrations of AHF 10-30 times higher than are present in whole plasma.

Unfortunately, the yield (AHF activity in the product/AHF activity in the starting plasma) obtained by use of this method is about 20%. This makes the cost of the factor excessive. In addition, the required infusion volume remains rather high (30 ml/1000 units of AHF), which again creates storage problems and makes at-home administration difficult, thus adding to the cost of therapy.

Furthermore, these concentrates contain less than 0.1% AHF protein and 99.9% contaminating proteins including specific blood-type antibodies that cause hemolysis, proteins that may cause immunologic abnormalities including an inversion of the T-cell ratio (helper/suppressor) which resembles AIDS, fibrinogen, fibronectin, von Willebrand factor and other proteins. Finally, the lyophilized concentrates are often contaminated with viruses (such as hepatitis B and non A/non B viruses or, possibly, viruses responsible for AIDS). Heating these preparations in the liquid state destroys most microorganisms, but also causes denaturation of a substantial portion of the AHF.

Chromatographic techniques (both ionic and hydrophobic chromatography) have been used, but only in the laboratory. Yield has been low (30-40% maximum) and resolution very poor.

Clearly, there is a need in the art for purer AHF preparations at a lower cost and a higher yield.

Attempts at satisfying this need include use of immunoaffinity chromatography using monoclonal antibodies: Zimmerman, et al, Characterization of the Human Factor VIII Procoagulant Protein with a Heterologous Precipitating Antibody, *Proc. Natl. Acad. Sci.* (U.S.A.) 79: 1648 (1982) and U.S. Pat. No. 4,361,509 (issued 11/30/82). Although these references report a 164,000-fold purification from plasma, the procedure involves six steps and the overall recovery is about 12% without a heating step.

J. J. Morgenthaler, Chromatography of Antihemophilic Factor on Diaminoalkane- and Aminoalkane-Derivatized sepharose, *Thromb. Haemostas.*, (Stuttgart) 47(2): 124 (1982) discloses use of acetate-lysine buffer on modified sepharose columns to purify Factor VIII:C from polyethylene glycol precipitated AHF. The authors indicate that hydrophobic rather than ionic forces govern the behavior of these chromatographic columns, but the reference is silent on yield, or purity of the product.

Austen, D. E. G. and Smith, J. K., Factor VIII Fractionation on Aminohexyl Sepharose with Possible Reduction in Hepatitis B Antigen, *Thromb. Haemostas.* (Stuttgart) 48(1): 46 (1982), disclose a method of processing plasma by aminohexyl sepharose column chromatography using 9×150 mm columns, acetate-lysine washing buffer and a saline gradient for elution. The reported maximum yield was 46% and the purity about 100-fold over plasma. The primary benefit of the procedure is said to be the ability to process larger samples. In addition, the authors report indications that the procedure slightly decreases contamination with Hepatitis B virus (by about 1.5 orders of magnitude, based on particle content).

A. Faure, et al, Improved Buffer for the Chromatographic Separation of Factor VIII Coagulant, *J. Chromatog.* 257: 387 (1983), disclose use of 1 and 10% saccharose in acetate-lysine buffers to improve the yield of Factor VIII during chromatography of cryoprecipitate on aminohexyl sepharose. The only buffer reported to be consistently effective in increasing Factor VIII separation from protein and recovery is one containing about 1% (0.03M) saccharose and 1% albumin. According to the authors, sugar was added to inhibit the formation of a molecular complex between Factor VIII and activated Factor IX and Factor X; albumin was added to eliminate non-specific adsorption. In one experiment, this buffer almost doubled the recovery of Factor VIII coagulant from plasma (not cryoprecipitate) over that obtained using either acetate lysine buffer alone, or acetate-lysine buffer with sacharose. However, the reported increase in recovery is difficult to interpret because absolute recovery figures are not given, nor are purity or resolution data. Use of sucrose alone did not result in a consistent increase in yield.

Lundblad, R. L. et al, The Effect of Dextrose on Chromatography of Antihemophilic Factor (Factor VIII), *Thrombosis Research,* 1: 197 (Pergamon Press, Inc. 1972), disclose that addition of 0.50M dextrose in the eluting buffer of bovine Factor VIII ion exchange column chromatography (on TEAE-cellulose) slightly improves the purity of the product and increases the yield of the peak fractions from 15-45% to 60-70%. However, the resolution was slightly reduced.

Neither Lundblad nor Faure use higher concentrations of sugar. Lundblad suggested that sucrose might bind to the cellulose matrix and prevent nonspecific adsorption of the protein. Faure suggested that sucrose addition might prevent complex formation between AHF and factors IXa and X. No substantiating evidence was given for either suggestion.

Arakawa, T. and Timasheff, S. N., Stabilization of Proteins by Sugars, *Biochem.* 21: 6536 (1982) disclose that many sugars cause preferential hydration of proteins in aqueous systems and, hence, serve to stabilize proteins in such systems. The article states that in sugar solutions, the equilibrium shifts towards a more tightly folded conformation. However, the article does not involve Factor VIII, nor protein purification, nor column chromatography. The disclosure of this article is incorporated by reference.

A variety of other articles disclose that sugars, polyhdric alcohols, amino acids or salts serve to stabilize proteins in aqueous systems: Arakawa, T. and Timasheff, S. N., Preferential Interactions of Proteins with Solvent Components in Aqueous Amino Acid Solutions, *Arch. Biochem. Biophys.* 224(1): 169 (1983); Pittz, E. P. and Timasheff, S. N., Interaction of Ribonuclease A with Aqueous 2-methyl-2,4-pentanediol at pH 5.8, *Biochem.* 17(4): 615(1978); Gekko, K. and Timasheff, S. N., Mechanism of Protein Stabilization by Glycerol: Preferential Hydration in Glycerol-Water Mixtures, *Biochem.* 20: 4667 (1981); Lee, J. C. and Timasheff, S. N., The Stabilization of Proteins by Sucrose, *J. Biol. Chem.* 256(14): 7193 (1981); Gekko, K. and Morikawa, T., Preferentail Hydration of Bovine Serum Albumin in Polyhydric Alcohol-Water mixtures, *J. Biochem.* 90: 39-50 (1981); and Arakawa, T. and Timasheff, S. N., Preferential Interactions of Proteins with Salts in Concentrated Solutions, *Biochem.* 21: 6545-6552 (1982). Again none of these articles disclose anything about protein or AHF purification, or column chromatography. The disclosures of these articles are incorporated by reference, however, because they contain techniques and data for determining preferential hydration of proteins that are useful in the practice of this invention. Pertinent excerpts of these disclosures have also been specifically incorporated in this application for convenient reference.

Finally, sugars and polyhydric alcohols have been used to preserve enzymatic or other activity of proteins and stabilize their structure after the proteins have been isolated from their native media. This procedure has been used during heating and lyophilization after purification.

As used in this application the following terms shall have the meanings ascribed to them below:

"Biological fluid" means any solution or suspension medium which contains or can contain a protein without causing its permanent denaturation or inactivation, including without limitation: plasma, urine, culture media, buffers and physiological solutions.

"Hydration additive" means individually or collectively sugars, polyhydric alcohols, amino acids and salts use of which in protein purification by chromatography increases yield, purity or resolution of the protein so purified. The use of this term is for convenience. Although the present inventors have observed a close correlation between optimization of the present process at specific levels of preferential hydration and have used protein hydration data as a marker for the amount of hydration additive used in the present invention, it is not to be assumed that hydration of a protein and improvement in its purification by chromatography are necessarily related as cause and effect.

OBJECTS OF THE INVENTION

It is accordingly an object of the present invention to provide a method for purifying AHF, and other proteins from biological fluids.

It is also an object of the present invention to provide a method for producing high-purity AHF and other protein preparations with a high yield over the starting material.

It is another object of the present invention to provide a method for obtaining AHF and other protein preparations having a higher concentration of AHF or other protein.

It is still another object of the present invention to provide a method for obtaining purified AHF (or other protein) preparations having a lower concentration of contaminating proteins.

It is another object of the present invention to lower the cost of purification of proteins and, in particular, of AHF.

It is yet another object of the present invention to provide a method for obtaining purified AHF and other protein preparations from previously contaminated biological fluids with a lower concentration of contaminating viruses.

It is a further object of the present invention to provide a method for obtaining AHF from plasma fractions using column chromatography; and, more generally, for obtaining proteins from biological fluids by column chromatography.

These and other objects and features of the present invention will become apparent to those of ordinary skill the the art in view of the following disclosure, accompanying claims and appended drawings, in which:

SUMMARY OF THE INVENTION

The present invention is directed to a process for purifying proteins by column chromatography in the presence of a sugar, polyhydric alcohol, amino acid or salt at a concentration sufficient to cause a substantial increase in at least one of yield, resolution and purity of the protein so-purified.

DETAILED DESCRIPTION OF THE INVENTION

As stated above, various sugars, polyhydric alcohols, amino acids and salts ("hydration additives") have been found to stabilize protein structure by preferential hydration of the proteins. An optimal increase in the preferential hydration parameter of the protein (or an optimal decrease in its preferential interaction parameter) in aqueous protein solutions is believed to promote protein aggregation and enhance folding of the protein molecule. It is further believed that, as a result, the hydrophobic groups are buried more tightly and the surface becomes more hydrophilic than in an aqueous solution alone.

The present inventors have found that exposure of proteins to the hydration additives causes the apparent ionic interaction of the protein to increase and the apparent hydrophobic interaction to decrease. The effect of these substances is reversible and depends on their concentration in the protein solution. The present invention uses this property of sugars, polyhydric alcohols, amino acids and salts to advantage in enhancing selective binding of proteins to an ionic column and selective elution of proteins from a hydrophobic affinity column.

First, the present invention is described by reference to a particularly preferred embodiment involving purification of AHF from cryoprecipitate by sequential processing first through an ion exchange chromatography column and then through a hydrophobic affinity chromatography column. However, the present invention is not limited to use of these chromatographic separations together, nor to purification of AHF alone. If desired, either chromatographic separation may be employed without the other and may be applied to purification of other difficult-to-purify proteins present not only in plasma, but in other biological or physiological fluids.

In accordance with a particularly preferred embodiment, cryo was prepared from plasma according to the well-known method of Newman, J., Johnson, A. J., Karpatkin, M. H. and Puszkin, S., *Brit. J. Haematol.* 21, 1 1971 as modified by Foster, P. R., Dickson, A. J., McQuillan, T. A., Dickson, I. H., Keddie, S., and Watt J. G., *Vox Sang.* 42, 180 (1982). The disclosure of these articles is hereby incorporated by reference. Briefly, frozen plasma was reduced to "snow" in a hammer mill, and thawed in a thawing vessel maintained at 15°-28° C. with stirring at 55 rpm. The thawed liquor and suspended cryoprecipitate was drained off by gravity and collected in a refrigerated centrifuge. The cryoprecipitate was recovered by centrifugation.

The cryo was dissolved in a buffer containing 0.02M tris(hydroxymethyl)aminomethane (Tris) pH 7.4, 0.02M sodium citrate, and 0.02M sodium chloride (NaCl) (Buffer I) at 1/10 of the starting volume. Aluminum hydroxide is optionally added to adsorb coagulation factors II, VII, IX, X and some fibrinogen, fibronectin and von Willebrand factor and the sample is then centrifuged to remove the hydroxide. The supernatant is collected.

Sorbitol is added to the sample until its concentration is 1M and the solution is acidified to pH 6.6 with 0.02M hydrochloric acid (HCl). Polyethylene glycol (PEG) is added to a final concentration of 4% to precipitate the fibrinogen, fibronectin, and Von Willebrand proteins. The solution is centrifuged and the supernatant saved for column chromatography.

Both QAE Sephadex A-25 resin and QAE-sepharose 4B—Fast Flow were obtained from Pharmacia Chemicals Inc., Piscataway, N.J.). The QAE sephadex A-25 is swelled in 0.5M NaCl overnight at room temperature (or for 1-2 hrs at near-boiling temperature) under gentle stirring. A volume in mls of swollen resin equal to about ⅔ the amount in mg of total protein present in the sample filtrate is packed into a column. (If QAE Sepharose Fast Flow is used, about ¼ of this amount would suffice).

A resin width-to-height ratio of about 2:1 is used in the column. The Sephadex resin is then washed with 5 volumes of 1M NaCl in 0.02M Tris (pH 7.4) 5 volumes of 0.5M NaCl in 0.02M Tris (pH 7.4), and finally with a 5 volumes of a buffer containing 0.02M Tris (pH 7.4), 0.15M NaCl, and 1M sorbitol (Buffer II).

The sample filtrate is loaded onto the column at a flow rate of about 1% of the column bed volume per minute and the column is washed with 2 volumes of Buffer II at a flow rate of about 3% of the column bed volume per minute. This is followed by a wash with 5 volumes of a buffer containing 0.02M Tris pH 7.4, 0.20M NaCl, and 1M sorbitol (Buffer III) and then with 2 volumes of 0.02M sodium acetate (NaAc) pH 6.0, 0.035M calcium chloride ($CaCl_2$) and 1M sorbitol (Buffer IV).

The AHF protein is eluted from the column with 2 volumes of a buffer containing 0.1M NaAc (pH 6.0), 0.25M $CaCl_2$, 10% glycerol, and 0.01%–0.05% Tween 80* (polysorbate 80; ICI, Wilmington, Del.) (Buffer V). The eluate is collected in fractions of 25% of the column bed volume and each fraction is assayed for AHF activity. The protein concentration in relevant fractions is determined according to a modified Bradford assay. (See Bradford, M. M., A Rapid and Sensitive Method for the Quantitation of Microgram Quantities of Protein Utilizing the Principal of Protein—Dye Binding, *Anal. Biochem.* 72: 248–254 (1976), the disclosure of which is hereby incorporated by reference.

* Use of Tween is particularly important with QAE-Sepharose 4B-Fast Flow to maximize yield.

The (QAE eluate) fractions containing AHF activity are pooled and diluted with 4 volumes of water.

Aminohexyl (AH) Sepharose resin (from Pharmacia Chemicals Inc., Piscataway, N.J.) is swelled overnight in 10 volumes of 0.5M NaCl. The swollen gel, in a ratio of 4 ml gel to 1000 units of AHF, is packed in a column with a width:height ratio of 1:1, and washed with 5 volumes of 0.02M NaAc (pH 6.0), 0.15M NaCl, and 0.002M $CaCl_2$ (Buffer VI).

The sample of diluted QAE eluate is loaded onto the column and washed with 10 volumes of Buffer VI, 5 volumes of a buffer containing 0.02M NaAc, pH 6.0, 0.35M NaCl, and 0.002M $CaCl_2$ (Buffer VII), and 2 volumes of a buffer containing 0.02M Tris, pH 7.4, 0.35M NaCl, and 0.002M $CaCl_2$ (Buffer VIII).

AHF is eluted with 2 volumes of a buffer (Buffer IX) containing 0.1M Tris (pH 7.4), 0.35M $CaCl_2$, 1M sorbitol, and 0.1% Tween 80 (polysorbate 80). The fractions are assayed for AHF activity and the active fractions are pooled.

The concentration of protein in the AHF-containing fractions are determined by the Weissman method. (Schaffner, W. and Weissman, C,, A Rapid, Sensitive and Specific Method for the Determination of Proteins in Dilute Solution *Anal. Biochem.* 56: 502–514 (1973), the disclosure of which is hereby incorporated by reference.) Briefly, the sample is precipitated with trichloroacetic acid to a final concentration of 15% (v/v) the precipitate is collected by filtration through a nitrocellulose filter. (Millipore HAWP produced by Millipore Corp., Medford, Mass.). The precipitate is stained with amido black and destained with a methanol-acetic acid-water mixture. The spots are cut out, eluted into 1 ml sodium hydroxide—EDTA (ethylenediamine tetraacetate) and read at $A_{630}$.

The QAE column may be regenerated by washing with a gradient of NaCl until 2M, then 0.1N NaOH to remove proteins, ethanol or non-ionic detergents to remove lipids, and finally with Buffer II to re-equilibrate.

The AH-Sepharose may be regenerated by washing with 1 volume $H_2O$, 2 volumes butanol, 1 volume 95% ethanol, 5 volumes 1M NaCl, 5 volumes 0.5M NaCl and 0.02M NaAC, pH 6.0, and 5 volumes of Buffer VI.

The resulting AHF from these sequential chromatography steps is high in yield, purity and concentration. A key feature of this invention is the use of hydration additives and the manipulation of their concentration in the purification of AHF and other proteins to promote the adsorption of AHF and other proteins to ion exchange resins, their desorption from hydrophobic affinity resins, and their recovery in high yield, resolution and purity.

The present inventors have found that use of hydration additives:

(a) significantly enhances the affinity of AHF to an anion exchange resin selectively allowing its retention over a rather narrow column band width; and (b) significantly destabilizes its affinity to hydrophobic resins allowing its ready elution.

The reasons for choosing this particular sequence of materials and steps in anion exchange chromatography are as follows:

(a) Loading the sample with Buffer II on an anion exchange column and washing with the same buffer permits AHF protein to bind ionically to the resin while allowing most other proteins to elute through. (Generally, the anion exchange column is able to achieve a higher initial purification than the hydrophobic affinity column). Buffer II contains the hydration additive at a concentration at which the AHF affinity for the column is stronger than that of many contaminating proteins.

(b) Buffer III washes off additional contaminating proteins from the resin.

(c) Buffer IV prepares AHF for elution by lowering the pH of the eluant closer to the isoelectric point of the AHF, thus selectively weakening its binding to the resin. However, to prevent band-broadening (and premature elution) by this buffer, the ionic strength of the solvent is simultaneously decreased.

(d) Buffer V contains: (i) a higher concentration of the buffering salt to ensure that all the protein is at the proper pH; (ii) calcium ions to elute the protein and to break non-covalent bonds between AHF and contaminating von Willebrand factor; (iii) glycerol to stabilize the protein (since the sugar was deleted to promote desorption of the protein from the resin); and (iv) Tween 80 to help eliminate non-specific binding of the protein to the gel matrix.

The aminohexyl column purifies AHF from contaminating hydrophilic proteins. In general, the resin binds proteins via hydrophobic interaction but the amino groups on the resin bind the protein through electrostatic interation. The reasons for the choice of steps and materials in this column are as follows:

(a) Buffer VI contains a moderate amount of salt to elute weakly bound proteins.

(b) Buffer VII contains a higher amount of salt to elute more tightly bound proteins.

(c) Buffer VIII raises the pH of the eluant to ionize a number of proteins so that they elute from the column. Although the charge of the AHF is increased at this pH, it remains bound to the column, albeit more loosely.

(d) Buffer IX elutes the AHF protein. The higher concentration of the buffering salt changes the pH. Calcium provides a counter-ion for elution and breaks non-covalent bonds to von Willebrand factor that may still be present. Sorbitol increases the ionic interaction and reduces the hydrophobic interaction of AHF for the column. Tween 80 helps eliminate hydrophobic and non-specific binding of the protein to the gel, and further increases the yield.

As stated above, the above-described method is only one preferred embodiment of the invention. Substantial purification of the AHF protein can be obtained by using either an anion exchange or a hydrophobic affinity column alone as described for the preferred embodiment. As persons of ordinary skill in the art will readily recognize, a number of modifications may be made without affecting the quality of the separation; a number of these are disclosed below.

(a) Crude AHF may be obtained by other known methods such as hydrophilic polymers (e.g. polyethylene glycol) which may be applied to the QAE column (at about 4–10 mg ml protein).

(b) Cryo can be reconstituted in any suitable buffer with a pH ranging from 5.0 to 9.0 (although 6.4–7.8 preferred and 7.0 is optimal). Aluminum hydroxide is not required. Any one of various physiological salts may be used in the buffer.

(c) A range of 1–6% of PEG can be used to precipitate the fibrinogen protein but this step is only important when the cryo has more than 6 mg of protein/ml solution. Alternatively, other hydrophilic polymers, or heparin may be used as the fibrinogen/fibronectin precipitating agent.

(d) Anion exchange resins or hydrophobic affinity resins from any manufacturer may be used. Although some buffer adjustment may be required with some resins having different charge densities, hydrophobicities or matrices than the resins employed here, the buffer changes may be readily made by one skilled in the art, and are usually included in the manufacturer's instructions. Maleic anhydride polyelectrolyte chromatography may be substituted for hydrophobic affinity chromatography. Further, it is not necessary that a hydrophobic column follow the anion exchange column. Other ion exchange columns or other partially hydrophobic columns may be used to further purify the material including, but not limited to maleic anhydride polyelectrolytes. In addition, as stated above, only one type of column (ion exchange, polyelectrolyte or hydrophobic affinity) may be used once, if desired.

(e) The protein to swollen QAE gel ratio may vary from 80:1 to 0.5:1, although the preferred range is 5:1 to 0.5:1 and the optimal range is 3:1 to 0.5:1.

(f) Various column dimensions may be used. The column width:height may vary from 1:100 to 100:1, although the preferred range is 1:1 to 5:1 and the optimal range is 2:1. One skilled in the art will recognize that resolution may change with different size columns, and that the buffer concentrations and elution volumes may have to be adjusted accordingly.

(g) There are no flow rate limitations other than column capacity. Generally, however, lower flow rates yield greater resolution.

(h) Washing with all of the Buffers II, III and IV is not absolutely essential. In addition, the amounts of each buffer used may vary. For Buffer II, the working range is from 0–10 or more column volumes, the preferred range is 2–5 volumes, and the optimal amount is 2 volumes. For Buffer III, the working range is from 0–10 or more volumes, the preferred range is 3–6 volumes, and the optimum is 5 volumes. For Buffer IV, the working range is 0–10 or more column volumes, the preferred range is 1–5 volumes, and the optimal is 2 volumes.

(i) A number of changes may be made in Buffer V without substantially reducing its eluting efficiency. The working pH range of the buffer is 4–9, the preferred range is 5.9–6.5 and the optimum is 6.0 (safe for AHF stability, but closer to the AHF isoelectric point). There are no limitations as to a particular buffer concentration although the preferred range is 0.02–2.0M, and the optimum is 0.35M. There are no limitations to a particular counter-ion except that its concentration be preferably at 0.02–2M and optimally at 0.35M for divalent ions and 1M for univalent ions. Any water miscible alcohol, or polyhydric alcohol, or water miscible organic solvent may be used although not absolutely required. Ethanol is preferred at amounts of 0.05–15%, and optimally at 1%. Any ionic or non-ionic detergent or surfactant, although not required, may be used. For Tween 80, the working range is 0–15%, the preferred range is 0.001–0.2%, and the optimum is 0.025%.

(j) The hydration additive concentration varies with the additive used.

(k) Alternative physiological buffers, suitable for parenteral administration, can be used (as is well within the skill of the art) within the above-indicated ranges for pH and ionic strength.

(l) It is necessary to ascertain the amount of sugars, polyhydric alcohols, amino acids or salts (hydration additives) to optimize AHF yield, purity, and resolution. While this may be done by trial and error, a starting point has been established with some sugars and alcohols in the case of AHF.

Since pure AHF was virtually unobtainable (certainly in amounts sufficient to generate preferential hydration data), the yield and purity of AHF with varying concentrations of hydration additives in aqueous solution, were correlated with the preferential hydration of bovine serum albumin (BSA) with varying concentrations of the same additives, in accordance with the data of Gekko, K. and Morikawa, T., supra. The data of Gekko and Morikawa are reproduced below:

TABLE I

Partial specific voulmes and preferential interaction parameters of bovine serum albumin with solvent components in water-polyhydric alcohol systems at 25° C.

| Alcohol % | $g_3{}^a$ | $\phi_2{}^0$ (ml/g) | $\phi_2'{}^0$ (ml/g) | $\left(\dfrac{\partial g_3}{\partial g_2}\right)_{T,\mu_1,\mu_3}$ (g/g) | $\left(\dfrac{\partial g_1}{\partial g_2}\right)_{T,\mu_1,\mu_3}$ (g/g) | $\left(\dfrac{\partial m_1}{\partial m_2}\right)_{T,\mu_1,\mu_3}$ (mol/mol) | $\left(\dfrac{\partial \mu_2}{\partial \mu_3}\right)_{T,P,m_2}{}^b$ |
|---|---|---|---|---|---|---|---|
| | | | | Water-ethylene glycol | | | |
| 0 | 0 | 0.734 ± 0.001 | 0.734 ± 0.001 | | | | |
| 20 (v/v) | 0.2768 | 0.733 ± 0.001 | 0.737 ± 0.001 | −0.041 ± 0.020 | 0.148 | 560 | 6,000 |
| 40 | 0.7312 | 0.733 ± 0.001 | 0.740 ± 0.001 | −0.097 ± 0.027 | 0.130 | 490 | 5,300 |
| 60 | 1.613 | 0.732 ± 0.001 | 0.744 ± 0.001 | −0.222 ± 0.041 | 0.137 | 520 | 5,500 |
| | | | | Water-glycerol | | | |
| 10 (v/v) | 0.1403 | 0.732 ± 0.001 | 0.736 ± 0.001 | −0.020 ± 0.010 | 0.143 | 540 | 5,700 |
| 20 | 0.3146 | 0.731 ± 0.002 | 0.740 ± 0.002 | −0.042 ± 0.023 | 0.165 | 620 | 6,600 |
| 30 | 0.5377 | 0.729 ± 0.001 | 0.744 ± 0.002 | −0.101 ± 0.020 | 0.187 | 710 | 7,600 |
| 40 | 0.8332 | 0.727 ± 0.001 | 0.746 ± 0.002 | −0.154 ± 0.024 | 0.185 | 700 | 7,400 |
| | | | | Water-xylitol | | | |
| 20 (w/v) | 0.2320 | 0.734 ± 0.001 | 0.742 ± 0.002 | −0.030 ± 0.021 | 0.129 | 490 | 5,200 |
| 30 | 0.3778 | 0.734 ± 0.001 | 0.747 ± 0.002 | −0.055 ± 0.011 | 0.146 | 550 | 5,800 |
| | | | | Water-mannitol | | | |
| 10 (w/v) | 0.1074 | 0.735 ± 0.001 | 0.742 ± 0.001 | −0.022 ± 0.006 | 0.205 | 770 | 8,300 |
| 15 | 0.1669 | 0.736 ± 0.001 | 0.746 ± 0.001 | −0.034 ± 0.007 | 0.204 | 770 | 8,200 |
| | | | | Water-sorbitol | | | |
| 5 (w/v) | 0.0518 | 0.736 ± 0.001 | 0.739 ± 0002 | −0.009 ± 0.009 | 0.174 | 660 | 7,000 |
| 10 | 0.1073 | 0.737 ± 0.001 | 0.744 ± 0.002 | −0.022 ± 0.009 | 0.205 | 770 | 8,300 |
| 15 | 0.1669 | 0.738 ± 0.001 | 0.748 ± 0.002 | −0.033 ± 0.010 | 0.198 | 750 | 8,000 |
| 20 | 0.2310 | 0.738 ± 0.001 | 0.753 ± 0.002 | −0.054 ± 0.001 | 0.229 | 870 | 4,400 |
| 30 | 0.3752 | 0.738 ± 0.002 | 0.761 ± 0.002 | −0.092 ± 0.016 | 0.245 | 930 | 9,900 |
| 40 | 0.5461 | 0.740 ± 0.002 | 0.768 ± 0.002 | −0.128 ± 0.018 | 0.234 | 880 | 9,400 |
| | | | | Water-inositol | | | |
| 5 (w/v) | 0.0516 | 0.732 ± 0.001 | 0.740 ± 0.001 | −0.021 ± 0.003 | 0.407 | 1,540 | 16,400 |
| 10 | 0.1063 | 0.729 ± 0.001 | 0.745 ± 0.001 | −0.041 ± 0.005 | 0.387 | 1,460 | 15,600 |

[a]Grams of alcohol per gram of water.
[b]Calories per mol of alcohol per mol of protein in 1.000 g $H_2O$.

TABLE III

Preferential Interaction Parameters of Proteins with Solvent Components in Aqueous Glucose Solutions

| [glucose] (M) | $\phi_2^0$ (mL/g) | $\phi'^0_2$ (mL/g) | $-\left(\frac{\partial g_3}{\partial g_2}\right)_{T,\mu_1,\mu_3}$ (g/g) | $\left(\frac{\partial g_1}{\partial g_2}\right)_{T,\mu_1,\mu_3}$ (g/g) | $-\left(\frac{\partial m_3}{\partial m_2}\right)_{T,\mu_1,\mu_3}$ (mol/mol) | $\left(\frac{\partial \mu_2}{\partial m_3}\right)^{exptl}_{T,P,m_2}$ [cal(mol of protein)$^{-1}$(mol of sugar)$^{-1}$] | $\left(\frac{\partial \mu_2}{\partial m_3}\right)^{calcd}_{T,P,m_2}$ [cal(mol of protein)$^{-1}$(mol of sugar)$^{-1}$] | $\dfrac{\left(\frac{\partial \mu_2}{\partial m_3}\right)^{exptl}_{T,P,m_2}}{\left(\frac{\partial \mu_2}{\partial m_3}\right)^{calcd}_{T,P,m_2}}$ |
|---|---|---|---|---|---|---|---|---|
| | | | | Chymotrypsinogen A, pH 2.0 | | | | |
| 0.5 | 0.725 | 0.737 | 0.0353 | 0.370 | 5.03 | 5600 | 10500 | 0.536 |
| 1.0 | 0.727 | 0.752 | 0.0802 | 0.394 | 11.4 | 6200 | 9300 | 0.668 |
| 1.5 | 0.729 | 0.758 | 0.103 | 0.317 | 14.5 | 5200 | 7900 | 0.657 |
| 2.0 | 0.726 | 0.760 | 0.138 | 0.297 | 19.7 | 5100 | 7000 | 0.725 |
| 3.0 | 0.727 | 0.760 | 0.168 | 0.205 | 24.0 | 3700 | 5700 | 0.656 |
| | | | | Lysozyme, pH 3.0 | | | | |
| 0.5 | 0.698 | 0.714 | 0.0456 | 0.458 | 3.69 | 4100 | 6900 | 0.599 |
| 1.0 | 0.699 | 0.720 | 0.0704 | 0.346 | 5.59 | 3000 | 5900 | 0.515 |
| 1.5 | 0.700 | 0.726 | 0.0958 | 0.294 | 7.60 | 2700 | 5200 | 0.515 |
| 2.0 | 0.703 | 0.728 | 0.101 | 0.215 | 8.01 | 2100 | 4600 | 0.450 |
| | | | | Ribonuclease A, pH 8.8 | | | | |
| 0.5 | 0.695 | 0.700 | 0.0157 | 0.164 | 1.19 | 1300 | 6600 | 0.202 |
| 1.0 | 0.695 | 0.707 | 0.0406 | 0.199 | 3.09 | 1700 | 5700 | 0.295 |
| 1.5 | 0.694 | 0.711 | 0.0580 | 0.178 | 4.41 | 1600 | 5000 | 0.312 |
| 2.0 | 0.700 | 0.716 | 0.0610 | 0.131 | 4.64 | 1200 | 4400 | 0.273 |
| | | | | Bovine Serum Albumin, pH 6.0 | | | | |
| 0.5 | 0.726 | 0.736 | 0.0295 | 0.308 | 11.1 | 12400 | 20100 | 0.618 |
| 1.0 | 0.726 | 0.741 | 0.0509 | 0.250 | 19.2 | 10400 | 17200 | 0.606 |
| 1.5 | 0.726 | 0.747 | 0.0737 | 0.226 | 27.8 | 9800 | 15100 | 0.649 |
| 2.0 | 0.727 | 0.750 | 0.0990 | 0.212 | 37.4 | 9600 | 13400 | 0.718 |
| | | | | Bovine Serum Albumin, pH 3.0 | | | | |
| 0.5 | 0.721 | 0.734 | 0.0377 | 0.394 | 14.2 | 15900 | | |
| 1.0 | 0.722 | 0.745 | 0.0755 | 0.371 | 28.5 | 15500 | | |
| 1.5 | 0.723 | 0.754 | 0.113 | 0.346 | 42.6 | 15000 | | |
| 2.0 | 0.728 | 0.759 | 0.137 | 0.294 | 51.7 | 13300 | | |

TABLE III

PROTEIN INTERACTIONS WITH AMINO ACIDS
PREFERENTIAL INTERACTION
PARAMETERS OF BSA WITH AMINO ACIDS

| Concentration | $g_3$ (g/g) | $\phi_2^{0a}$ (ml/g) | $\phi_2'^0$ (ml/g) | hydration $(\delta g_3/\delta g_2)_{T,\mu_1,\mu_3}$ (g/g) | hydration $(\delta_1/\delta_2)_{T,\mu_1,\mu_3}$ (g/g) |
|---|---|---|---|---|---|
| | | | Glycine | | |
| 0.7 | 0.0546 | 0.737$^b$ | 0.747 ± 0.001 | −0.0245 ± 0.0026 | 0.450 ± 0.0047 |
| 1.4 | 0.112 | 0.720$^b$ | 0.752 ± 0.001 | −0.0463 ± 0.0028 | 0.412 ± 0.025 |
| 2.0 | 0.165 | 0.735$^b$ | 0.758 ± 0.001 | −0.0687 ± 0.0030 | 0.416 ± 0.018 |
| | | | β-Alanine | | |
| 0.7 | 0.0653 | 0.736$^b$ | 0.744 ± 0.001 | −0.0238 ± 0.0032 | 0.365 ± 0.049 |
| 1.0 | 0.0949 | 0.736 ± 0.001 | 0.744 ± 0.001 | −0.0250 ± 0.0066 | 0.263 ± 0.069 |
| 1.4 | 0.137 | 0.738$^b$ | 0.749 ± 0.001 | −0.0384 ± 0.0084 | 0.281 ± 0.025 |
| | | | α-Alanine | | |
| 0.7 | 0.0653 | 0.738$^b$ | 0.740 ± 0.001 | −0.0184 ± 0.0034 | 0.282 ± 0.052 |
| 1.0 | 0.0951 | 0.738$^b$ | 0.748$^b$ | −0.0364 | 0.383 |
| 1.4 | 0.137 | 0.737 ± 0.001 | 0.749 ± 0.001 | −0.0451 ± 0.0075 | 0.329 ± 0.055 |
| | | | Betaine | | |
| 0.7 | | 0.737$^b$ | 0.744$^b$ | −0.0463 | 0.525 |
| 1.4 | 0.191 | 0.736 ± 0.001 | 0.751 ± 0.001 | −0.0948 ± 0.0144 | 0.497 ± 0.076 |
| 2.0 | 0.292 | 0.736$^b$ | 0.752$^b$ | −0.125 | 0.428 |

| Concentration | $(\delta m_1/\delta m_2)_{T,\mu_1,\mu_3}$ (mol/mol) | $(\delta\mu_2/\delta m_3)_{T,P,m_2}$ (cal/mol protein/mol amino acid) | $(\delta\mu_2/\delta m_3)_{T,P,m_2}$ (cal/mol protein/mol amino acid) | $(\delta\mu_2/\delta m_3)^{exp}/(\delta\mu_2/\delta m_3)$ |
|---|---|---|---|---|
| | | Glycine | | |
| 0.7 | −22.2 ± 2.3 | 17,800 ± 1900 | 18,000 | 0.96 |
| 1.4 | −41.9 ± 2.5 | 16,300 ± 1000 | 18,000 | 0.87 |
| 2.0 | −62.2 ± 2.7 | 16,500 ± 700 | 18,800 | |
| | | β-Alanine | | |
| 0.7 | −10.2 ± 2.4 | 14,500 ± 1900 | | |
| 1.0 | −19.1 ± 5.0 | 10,400 ± 2700 | | |
| 1.4 | −29.3 ± 2.6 | 11,100 ± 1000 | | |
| | | α-Alanine | | |
| 0.7 | −14.0 ± 2.6 | 11,100 ± 2100 | 16,000 | 0.69 |
| 1.0 | −27.9 | 15,200 | 16,000 | 0.96 |
| 1.4 | −34.4 ± 5.7 | | 16,000 | 0.81 |
| | | Betaine | | |
| 0.7 | −26.9 | 20,800 | | |
| 1.4 | −36.0 ± 0.4 | 20,000 ± 3100 | | |
| 2.0 | −72.5 | 17,000 | | |

$^a$ = 0.734 in 0.2 M NaCl (36).
$^b$Standard deviations were less than 0.0005 ml/g.

TABLE I
Interaction Parameters

| condition | $g_3$(g/g) | $\bar{v}_3$ (mL/g) | $\phi_2^0$ (mL/g) | $\phi'_2{}^0$ (mL/g) | $\left(\frac{\partial g_3}{\partial g_2}\right)_{T,\mu_1,\mu_3}$ (g/g) | $A_3$ (g/g) | $\left(\frac{\partial g_1}{\partial g_2}\right)_{T,\mu_1,\mu_3}$ (g/g) |
|---|---|---|---|---|---|---|---|
| *Lysozyme* | | | | | | | |
| 0.02 M acetate, pH 4.5 | | | 0.714 ± 0.002 | 0.712 ± 0.001 | | | |
| 0.5 M acetate, pH 4.68 | 0.0431 | 0.502 | 0.712 ± 0.002 | 0.726 ± 0.001 | −0.0295 ± 0.0063 | | 0.684 ± 0.147 |
| 1 M acetate, pH 4.71 | 0.0906 | 0.516 | 0.712 ± 0.002 | 0.731 ± 0.001 | −0.0433 ± 0.0068 | | 0.478 ± 0.075 |
| 1 M NaCl, pH 4.5 | 0.0597 | 0.331 | 0.707 ± 0.002 | 0.723 ± 0.002 | −0.0253 ± 0.0063 | | 0.424 ± 0.106 |
| *Bovine Serum Albumin* | | | | | | | |
| 0.02 M acetate, pH 4.5 | | | 0.735 ± 0.001 | 0.736 ± 0.001 | | | |
| 0.5 M Na$_2$SO$_4$, pH 4.5 | 0.0718 | 0.165 | 0.734 ± 0.001 | 0.750 ± 0.001 | −0.0206 ± 0.0026 | | 0.287 ± 0.036 |
| 0.5 M Na$_2$SO$_4$, pH 7.0 | 0.179 | 0.165 | 0.735 ± 0.002 | 0.758 ± 0.001 | −0.0298 ± 0.0039 | | 0.414 ± 0.054 |
| 1 M Na$_2$SO$_4$, pH 4.5 | 0.145 | 0.208 | 0.735 ± 0.002 | 0.781 ± 0.001 | −0.0669 ± 0.0044 | | 0.459 ± 0.030 |
| 1 M Na$_2$SO$_4$, pH 5.6 | 0.141 | 0.208 | 0.735 ± 0.001 | 0.788 ± 0.001 | −0.0739 ± 0.0028 | | 0.524 ± 0.020 |
| 1 M NaCl, pH 4.5 | 0.0596 | 0.331 | 0.734 ± 0.001 | 0.744 ± 0.001 | −0.0158 ± 0.0032 | | 0.265 ± 0.053 |
| 1 M NaCl, pH 5.6 | 0.0597 | 0.331 | 0.735 ± 0.001 | 0.744 ± 0.001 | −0.0145 ± 0.0032 | | 0.243 ± 0.054 |
| 1 M CaCl$_2$, pH 5.6 | 0.114 | 0.216[1] | 0.734 ± 0.001 | 0.731 ± 0.001 | 0.00367 ± 0.00245 | 0.0380 | −0.0321 ± 0.0214 |
| 1 M KSCN, pH 5.6 | 0.102 | 0.530 | 0.738 ± 0.001 | 0.735 ± 0.001 | 0.00706 ± 0.00471 | 0.0378 | −0.0689 ± 0.0459 |
| 0.5 M MgCl$_2$, pH 4.5 | 0.0479 | 0.150 | 0.733 ± 0.001 | 0.737 ± 0.001 | −0.00491 ± 0.00245 | 0.0095 | 0.102 ± 0.051 |
| 1 M MgCl$_2$, pH 5.6 | 0.0975 | 0.176 | 0.737 ± 0.001 | 0.740 ± 0.001 | −0.00416 ± 0.00277 | 0.0251 | 0.0427 ± 0.0285 |
| 1 M MgSO$_4$, pH 4.5 | 0.121 | 0.136 | 0.734 ± 0.001 | 0.769 ± 0.001 | −0.0469 ± 0.0027 | | 0.388 ± 0.0222 |

[a] Dunn (1966).

TABLE II
Partial Specific Volumes and Preferential Interaction Parameters of Proteins in Aqueous Lactose Solutions

| [lactose] (M) | $\phi_2^0$ (mL/g) | $\phi'_2{}^0$ (mL/g) | $-\left(\frac{\partial g_3}{\partial g_2}\right)_{T,\mu_1,\mu_3}$ (g/g) | $-\left(\frac{\partial m_3}{\partial m_2}\right)_{T,\mu_1,\mu_3}$ (mol/mol) | $g_3$(g/g) | $\left(\frac{\partial g_1}{\partial g_2}\right)_{T,\mu_1,\mu_3}$ (g/g) | $\left(\frac{\partial \mu_3}{\partial m_3}\right)_{T,P,m_2}$ [cal (mol of protein)$^{-1}$ (mol of sugar)$^{-1}$] |
|---|---|---|---|---|---|---|---|
| *Ribonuclease A, pH 8.8* | | | | | | | |
| 0 | 0.691 | 0.692 | | | | | |
| 0.2 | 0.692 ± 0.002 | 0.696 ± 0.001 | 0.0115 ± 0.0082 | 0.460 ± 0.329 | 0.072 | 0.160 ± 0.115 | 1300 ± 900 |
| 0.3 | 0.692 | 0.701 ± 0.001 | 0.0241 ± 0.0028 | 0.967 ± 0.112 | 0.110 | 0.220 ± 0.026 | 1800 ± 200 |
| 0.4 | 0.693 ± 0.002 | 0.704 ± 0.002 | 0.0343 ± 0.0118 | 1.37 ± 0.47 | 0.150 | 0.229 ± 0.079 | 1800 ± 650 |
| *Chymotrypsinogen A, pH 2.0* | | | | | | | |
| 0 | 0.730 | 0.731 | | | | | |
| 0.1 | 0.729 ± 0.001 | 0.736 ± 0.001 | 0.0191 ± 0.0052 | 1.43 ± 0.39 | 0.035 | 0.545 ± 0.149 | 8200 ± 2000 |
| 0.2 | 0.727 ± 0.002 | 0.740 ± 0.002 | 0.0354 ± 0.0109 | 2.66 ± 0.82 | 0.072 | 0.495 ± 0.152 | 7400 ± 2300 |
| 0.3 | 0.727 ± 0.001 | 0.744 ± 0.002 | 0.0483 ± 0.0085 | 3.63 ± 0.64 | 0.110 | 0.440 ± 0.007 | 6600 ± 1200 |
| 0.4 | 0.728 | 0.753 ± 0.002 | 0.0743 ± 0.0059 | 5.58 ± 0.44 | 0.149 | 0.499 ± 0.040 | 7500 ± 600 |
| 0.47 | 0.729 ± 0.001 | 0.756 ± 0.002 | 0.0818 ± 0.0091 | 6.14 ± 0.68 | 0.179 | 0.457 ± 0.051 | 5900 ± 800 |
| *Bovine Serum Albumin, pH 6.0* | | | | | | | |
| 0 | 0.729 | 0.728 | | | | | |
| 0.1 | 0.729 ± 0.001 | 0.733 ± 0.001 | 0.0109 ± 0.0053 | 2.17 ± 1.03 | 0.035 | 0.311 ± 0.151 | 12300 ± 6000 |
| 0.3 | 0.725 ± 0.001 | 0.736 ± 0.001 | 0.0300 ± 0.0057 | 5.97 ± 1.14 | 0.110 | 0.273 ± 0.052 | 10800 ± 2100 |
| 0.4 | 0.725 ± 0.002 | 0.742 ± 0.003 | 0.0482 ± 0.0149 | 9.63 ± 2.96 | 0.150 | 0.321 ± 0.099 | 12700 ± 4000 |

One of ordinary skill in the art can generate yield and purity chromatography data for the protein desired to be purified, AHF in this case, by using various hydration additives at concentrations shown to produce preferential hydration values of 0.23 with bovine serum albumin.

Using the hydration values for BSA in solutions containing various sugars, the following observations were made:

When the values for preferential hydration of BSA were plotted against the yield and purity of AHF obtained by chromatography of cryo in the presence of a variety of sugars and polyhydric alcohols at different concentrations, the yield (FIG. 1) and purity (FIG. 2) of the factor were found to be maximized over the relatively narrow sugar concentration range that produced a preferential hydration of BSA of 0.22–0.24 g $H_2O$/g BSA. At concentrations of sugar that produced a preferential hydration of BSA higher or lower than this value, the yield and purity of the isolated AHF were lower. 1M sorbitol provided the optimal sorbitol concentration for AHF purification.

An amount of any hydration additive able to preferentially hydrate the AHF may be used although amounts that would preferentially hydrate BSA at 0.230 gms H₂O/gm BSA have been found to be optimal. The hydration additive used need not be sorbitol, although it is preferred.

Sugars that can be used (not only for AHF, but also for other proteins) are sucrose, maltose, lactose, glucose, ribose, arabinose, galactose, fructose, mannose, rhamnose, malezitose, dextran, xylose, allose, 6-deoxymannose, 6-deoxy-galactose et al. Preferably, it should be possible for humans to metabolize the sugar to eliminate a further purification step. Preferred for AHF purification are glucose and maltose. For AHF purification, some of the preferred concentration ranges are:

sucrose 0.5 to 2.0M with 1.0M being most preferred;
lactose 0.0–0.4M with 0.25 being most preferred;
maltose 0.2–0.40M with 0.3M most preferred; and
glucose 0.5 to 2.0M with 1.0M being most preferred.

Alternatively, another polyhydric alcohol, an amino acid, or a salt can be used.

In general, suitable polyhydric alcohols are sorbitol, mannitol, inositol, adonitol, erythritol, ethylene glycol, xylitol, propylene glycol, 2-methyl-2,4-pentanediol, ficoll (a synthetic sucrose polymer) and ribitol, with sorbitol being most preferred. The preferred concentration range for sorbitol in AHF chromatography is 0.5 to 2.0M with 1.0M being most preferred.

Suitable amino acids are glycine, beta alanine, alpha alanine and preferably betaine.

Suitable salts are sodium and potassium acetate, sodium chloride, sodium sulfate, calcium and magnesium chloride, magnesium sulfate, potassium thiocyanate at al. The preferential hydration parameters may be obtained for a variety of sugars, alcohols, amino acids and salts from the above-cited articles by Timasheff et al., or may be determined empirically by their methods.

The foregoing references disclose preferential interaction or preferential hydration (both terms are defined below) values for a variety of proteins using a variety of solvents, and methods for determining preferential hydration. The hydration values and concentrations of the hydration additives disclosed in these references have been reproduced below:

Since the method described in Lee, et al and Arakawa, et al., supra is a complicated procedure and requires a high degree of physicochemical expertise, it may be possible to determine the approximate concentration of the additive required to reach the desired preferential interaction or preferential hydration by ascertaining whether it had been used previously by these investigators with a bovine albumin system or with another protein.

As stated above for AHF, BSA was used as the model. It was found that the amount of an additive that would preferentially hydrate the albumin to a level of approximately 0.22–0.24 (gH₂O)/(gBSA) was the optimum for AHF chromatography.

After the hydration values have been obtained from the above tabulated data, it will still be important to ascertain the optimal concentration for the particular protein employed by varying the amount of additive used during chromatography (within a moderate range of the concentration as indicated by the preferential hydration of the albumin) because each protein interacts differently with each additive. Reference to the albumin only provides a starting point for determination of the hydration additive concentration that will be used in the chromatography of AHF.

Alternatively, the method of Lee et al could be employed to determine the preferential hydration parameters of the protein of choice and the concentration of sugars, polyhydric alcohols or amino acids would have to be optimized in the chromatographic system where it was employed.

The Lee et al. procedure is a study of the preferential binding of solvent components to protein in a water-sugar (polyhydric alcohol, a.a., etc.) mixture, where water is component 1, protein is component 2, and sugar (or other hydration additive), etc. is component 3. These interactions are measured by following the changes in partial specific volume of the protein as a function of hydration additive concentration. Partial specific volumes are obtained from density measurements made with a precision Density Meter DMA-02 (Anton Paar, Gratz) by:

$$\phi = 1/_o \left( 1 - \frac{\rho - \rho_o}{C} \right) \quad (1)$$

where
$\phi$ = apparent partial specific volume
$\rho + \rho_o$ = density of solution plus solvent, respectively
$C$ = concentration of protein in grams/ml.

Since densities of the proteins are measured at conditions of both constant chemical potential and constant molality of the solvent components, it becomes possible to determine the extent of preferential interaction between components 3, 2 and 1.

$(\partial g_3 / \partial g_2)_{T,\mu_1,\mu_3} \equiv \xi_3$ (preferential interaction parameter)

$\xi_3$ is related to the change of density ($\rho$) of the system by:

$$\xi_3 = (\partial g_3 / \partial g_2)_{T,\mu_1,\mu_3} = \frac{(\partial \rho / \partial g_2)_{T,\mu_1,\mu_3} - (\partial \rho / \partial g_2)_{T,p,m_3}}{(\partial g / \partial g_3)_{T,p,m_2}}$$

where
$m_i$ is the molal concentration of component i;
$u_i$ is its chemical potential;
$T$ = thermodynamic temperature;
$P$ = pressure;
$g_i$ = concentration of component i in grams/g H₂O.

From the definition of partial specific volume at infinite dilution one can write:

$$(1 - \phi'_2 \rho_o)^o = (1 - \phi^*_2 \rho_o)^o + \xi_3 (1 - \bar{v}_3 \rho_o) \quad (2)$$

where superscript o indicates infinite dilution of macromolecular species.
$\bar{v}_3$ = partial specific volume of component 3;
$\rho_o$ = density of solvent;
$\phi^*_2$ = apparent partial specific volume of the protein; measured under conditions of constant molality;
$\phi'_2$ = apparent partial specific volume of protein measured at constant chemical potential.

The sign of $(\partial g_3 / \partial g_2)_{T,\mu_1,\mu_3}$ may be positive which means preferential binding of component 3 to protein, or negative which means a deficiency of component 3 around the protein and thus preferential interaction with water. When the sign is negative, the preferential hydration parameter is given by $$(\partial g_1/\partial g_2)_{T,\mu_1,\mu_3} = -1/g_3(\partial g_3/\partial g_2)_{T,\mu_1,\mu_3} \quad (3)$$

Measurements are carried out with the precision density meter and the apparent partial specific volume ($\phi$) calculated with Equation 1. The observed extrapolated values of $\phi$ are then plotted as a function of protein concentration and the extrapolated value at infinite dilution, and employed in Equation 2 to calculate extent of preferential interaction. Then, the preferential hydration parameter may be calculated using Equation 3.

Using the invention as described has resulted in purification levels of AHF protein between 100–150 times greater than the prior art, and the recovery of AHF in much higher yields. The invention is further described by the following Examples. These Examples are intended to illustrate the invention without limiting its scope.

EXAMPLE 1

3 liters of frozen human plasma were allowed to partially soften and were then crushed with a rubber mallet. The crushed material was allowed to thaw at 37° C. while maintaining the temperature of the plasma at 0°–2° C.; it was then immediately placed in an ice bath. It was then centrifuged at 2500×g at 4° C. for 0.5 hrs. The precipitate was reconstituted in 300 mls of Buffer II, and a 1.3% aluminum hydroxide suspension (30 mls/liter of plasma) was added. The mixture was then spun at 10° C. at 2500×g for 15 minutes. Upon assay of the supernatant, the protein and AHF concentrations were found to be about 4 mg/ml and 2.8 units/ml respectively. This gave a total protein and AHF amount of 1200 mgs and 840 units, respectively.

A column containing 800 mls of QAE-Sephadex A25 swollen resin was prepared. The column width:height was 2:1. The 300 mls of sample supernatant were loaded onto this column at a flow rate of 12 ml/min. The column was then washed with 2 volumes of Buffer II, 5 volumes of Buffer III, 2 volumes of Buffer IV and 2 volumes of Buffer V, at a flow rate of 24 mls/min. (Higher concentrations of salts were required with QAE-Sepharose 4B—fast flow for optimal purity and yield). The eluate was collected with Buffer V as follows:

| Fraction No. | Factor VIII:C (Units/ml) | Factor VIII:C (Units/tube) | Total Protein (mg/ml) |
| --- | --- | --- | --- |
| 1 | 0 | 0 | 0 |
| 2 | 0 | 0 | 0 |
| 3 | 0.09 | 10.8 | — |
| 4 | 0.74 | 88.8 | — |
| 5 | 1.80 | 252.0 | 0.075 |
| 6 | 1.30 | 169.0 | 0.045 |
| 7 | 1.40 | 168.0 | 0.004 |
| 8 | 0.75 | 90.0 | — |
| 9 | 0.41 | 49.0 | — |

Total AHF Content in Product: 827 units, 0.124 mg total protein/ml
Purification: 3200-fold from cryoprecipitate
Recovery: 98%

Fractions 5–7 representing 70% recovery and 2600 fold purification were pooled to give a volume of 390 ml. This solution was diluted with 4 volumes of Buffer VI to give a total volume of 1950 ml.

Four mls of swollen AH-sepharose were packed into a small column whose width:height ratio was 1:1. The Factor VIII:C-containing solution from QAE purification was loaded onto the column at a flow rate of 24 mls/min. The column was then washed with 10 volumes of Buffer VI, 5 volumes of Buffer VII, 2 volumes of Buffer VIII, and 2 volumes of Buffer IX. The flow rate was 24 mls/min. One ml fractions were collected during elution with Buffer.

| IX. The results are shown below. | | |
| --- | --- | --- |
| Fraction No. | Units/ml | mg/ml |
| 1 | 0 | — |
| 2 | 194 | 0.434 |
| 3 | 239 | 0.406 |
| 4 | 84 | 0.196 |
| 5 | 46 | 0.182 |
| 6 | 15 | 0.168 |
| 7 | 5 | 0.056 |
| 8 | 0 | 0.028 |

Total (this step)        577 units, 1.47 mgs
Purification (this step) 11-fold
Overall Purification     28,000-fold over plasma
Recovery (this step)     98%
Overall Recovery         about 70%

In the above Example, only three fractions were used for hydrophobic affinity chromatography. This was done to maximize resolution and purity. If yield is maximized, all of the active fractions from QAE chromatography may be used. On the basis of this and other data, the overall recovery would have been 96%.

EXAMPLES 2–6

Cryo was eluted from QAE columns as described in Example 1. The purification and recovery results are shown below.

| Example | Purity (over Plasma) | Recovery (%) |
| --- | --- | --- |
| 2 | 3500× | 100 |
| 3 | 6200× | 100 |
| 4 | 5300× | 99 |
| 5 | 4500× | 79 |
| 6 | 3700× | 100 |
| average | 4640× | 95.6 |

EXAMPLES 7–9

Cryo was eluted from QAE columns as described in Example 1 except that sorbitol was omitted. The results are shown below.

| Example | Purity (over Plasma) | Recovery (%) |
| --- | --- | --- |
| 7 | 1400× | 69 |
| 8 | 2500× | 49 |
| 9 | 2900× | 59 |
| average | 2300× | 59 |

EXAMPLES 14–22

Cryo was purified by QAE chromatography as described in Example 1 except that different sugars were used. As stated above, preferential hydration experiments could not be carried out with Factor VIII, so the data obtained from Arakawa, Gekko and Morikawa with BSA were used instead. (See the Preferential Hydration Tables above).

The results are shown below.

| Example | Bovine Serum Albumin (BSA) | | | Factor VIII | |
|---|---|---|---|---|---|
| | Sugar | (Molarity) | (Pref. Hydration) | (Percent Recovery) | (Purity over Plasma) |
| 14 | lactose | 0.25 | 0.300 | 85 | 4400× |
| 15 | lactose | 0.20 | 0.300 | 70 | 2700× |
| 16 | glucose | 1.0 | 0.250 | 83 | 5100× |
| 17 | sorbitol | 1.6 | 0.235 | 88 | 2700× |
| 18 | sorbitol | 1.1 | 0.229 | 100 | 5500× |
| 19 | glucose | 1.5 | 0.226 | 100 | 6100× |
| 20 | glucose | 2.0 | 0.212 | 76 | 4900× |
| 21 | sorbitol | 0.55 | 0.205 | 62 | 1700× |
| 22 | sorbitol | 0.82 | 0.198 | 72 | 1900× |

Figure 1:
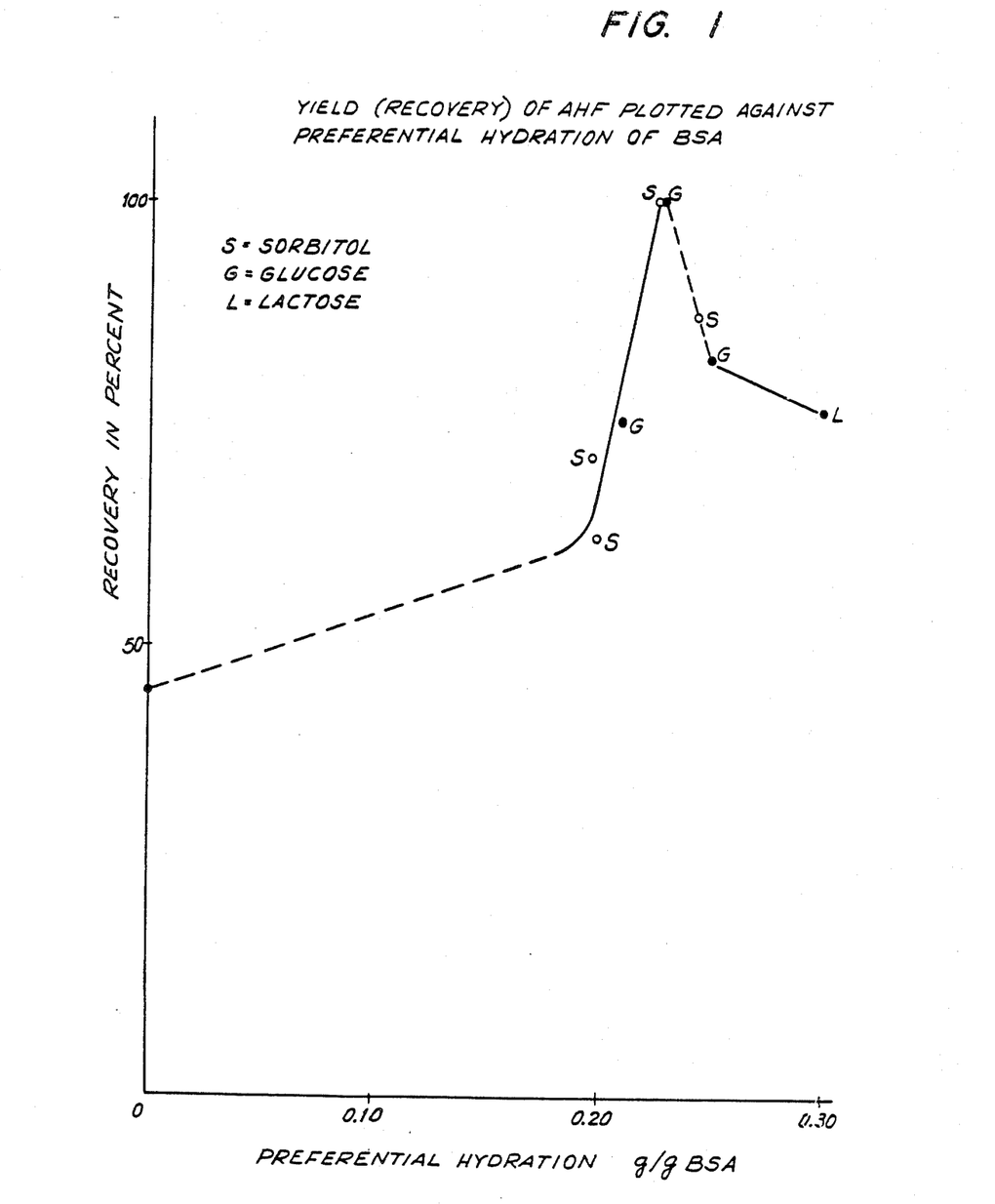
FIG. 1 is a graph of AHF yield plotted against preferential hydration of bovine serum albumin (BSA) with various sugars.
Figure 2:
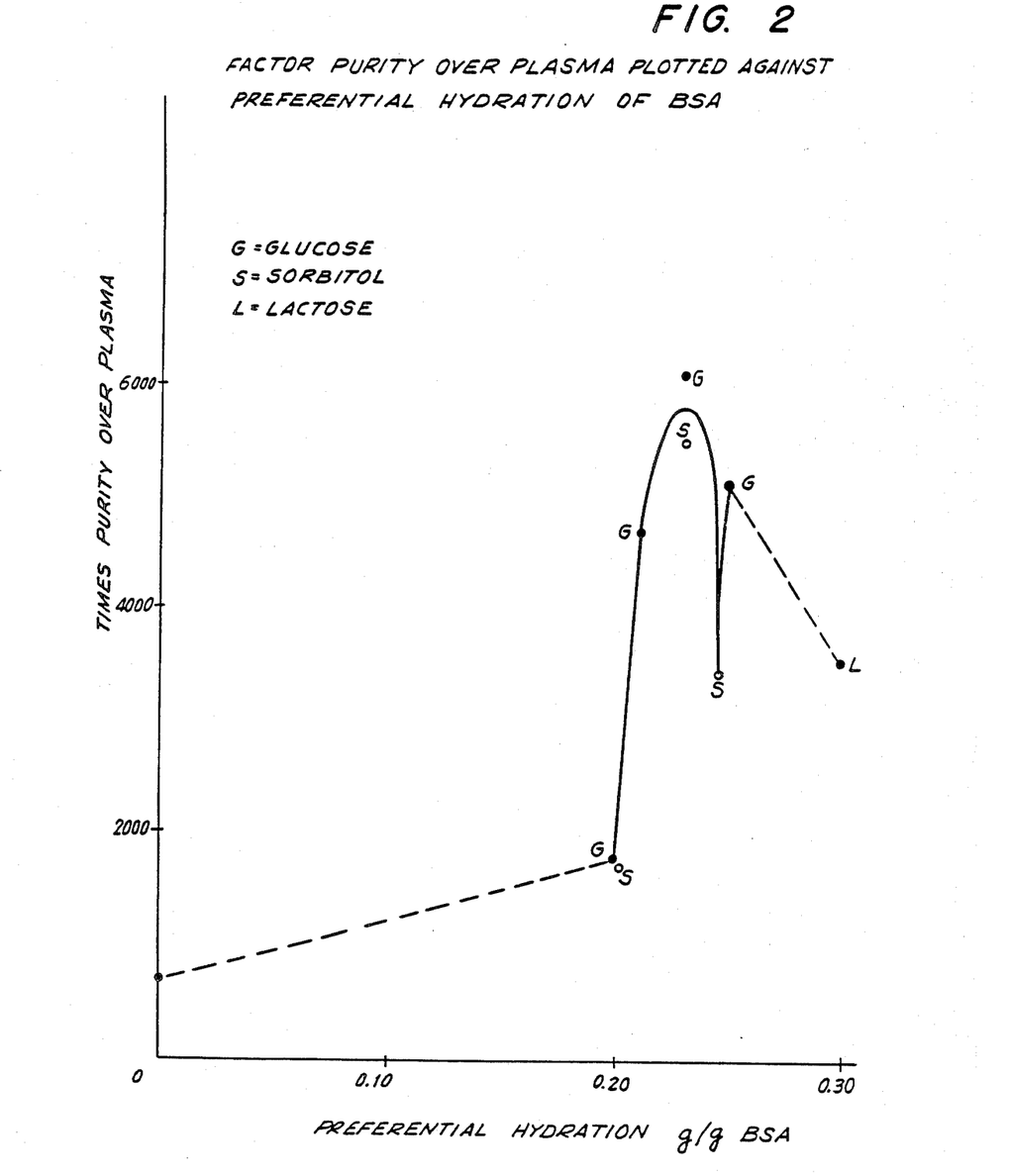
FIG. 2 is a graph of AHF purity over plasma plotted against preferential hydration of BSA with various sugars.
Figure 3:
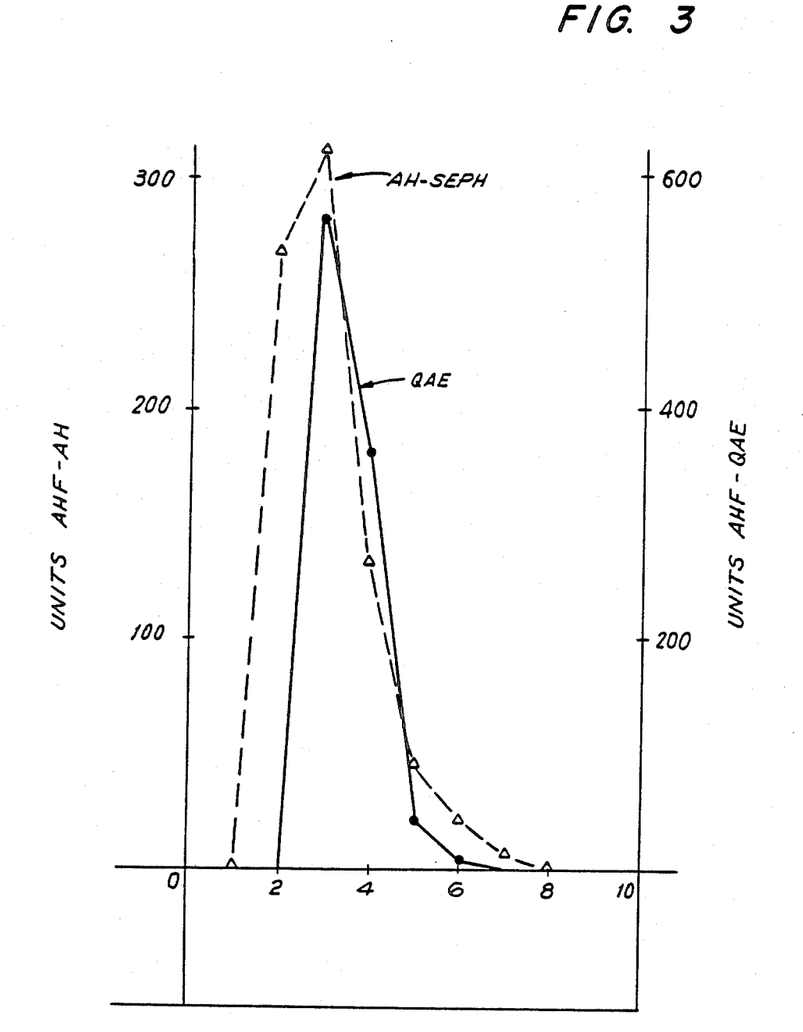
FIG. 3 is a graph of AHF resolution obtained by use of QAE-Sephadex anion exchange chromatography and aminohexyl sepharose affinity chromatography.

When the values for purity and yield of AHF were plotted against the values for preferential hydration of BSA with equivalent amounts of sugar, an optimum peak was observed for each (FIGS. 1 and 2).

EXAMPLE 23

Cryo was purified by QAE chromatography as described in Example 1, with or without sorbitol. The results were as follows:

| Sorbitol (Molarity) | Recovery (%) | Purity (over Plasma) |
|---|---|---|
| 1 | 77 | 4200× |
| 1 | 82 | 3700× |
| 1 | 100 | 5600× |
| 1 | 92 | 4000× |
| 1 | 98 | 9000× |
| 1 | 94 | 3900× |
| 1 | 91 | 3400× |
| 0 | 35 | 560× |
| 0 | 48 | 535× |
| 0 | 59 | 683× |
| 0 | 59 | 1800× |
| 0 | 71 | 700× |

EXAMPLE 24

Cryo was purified by QAE chromatography as described in Example 1, except that maltose was employed at different concentrations. The results were as follows:

| Maltose (M) | Recovery (%) | Final Purity (over Starting Plasma) |
|---|---|---|
| 0.3 | 100 | 2100× |
| 0.3 | 81 | 1420× |
| 0.3 | 100 | 2200× |
| 0.3 | 100 | 7500× |
| 0.0 | 64 | 3400× |
| Washing buffer: 0.05 M CaCl$_2$ 0.02 M NaAC | | |
| 0.3 | 100 | 3600× |
| 0.3 | 88 | 8000× |
| 0.3 | 100 | 3000× |
| Washing buffer: 0.02 M NaAC; 0.035 M CaCl$_2$ | | |
| 0.3 | 92 | 4000× |
| 0.3 | 91 | 18000× |
| 0.3 | 98 | 9000× |
| 0.0 | 71 | 700× |
| 0.0 | 78 | 560× |
| 0.3 | 94 | 3900× |

EXAMPLE 25

QAE eluate was processed by aminohexyl sepharose chromatography as described in Example 1, except that sorbitol was omitted. The results are as follows:

| Sorbitol (Molarity in Eluate) | QAE Eluate | | |
|---|---|---|---|
| | (Purity over Starting Plasma) | (Recovery) | (Final Purity over Starting Plasma) |
| 0 | 2000× | 13% | 1800× |
| 0 | 2100× | 48% | 2300× |
| 1 | 4400× | 100% | 38,100× |
| 1 | 4500× | 96% | 38,000× |
| 1 | 5700× | 89% | 25,000× |
| 1 | 2100× | 100% | 20,700× |
| 1 | 5600× | 94% | 80,000× |
| 1 | 5700× | 60% | 17,000× |

EXAMPLE 26

Cryo prepared according to Example 1 was processed by maleic anhydride polyelectrolyte chromatography in accordance with Example 1. The maleic anhydride polyelectrolyte can be obtained from Speywood in Wrexham, Wales, England (sold under the trademark SPEYLITE). The use of maleic anhydride polyelectrolytes in AHF purification has been described in Johnson, A. J., et al J. Lab. Clin. Med. 92(2): 194–210 (August 1978).

The polyelectrolyte resin was prepared as follows:

Dry resin was soaked in 0.15M NaCl (30 min), the pH was lowered to 4.0 with citric acid, maintained for 20 minutes, then raised to 6.6 with NaOH.

Chromatography took place as follows:

The column was equilibrated with 5 col. volumes of 0.15M NaCl, 0.02M sodium citrate (pH 6.6). The AHF concentrate was adjusted to pH 6.6 with citric acid and applied to the column at a rate of 1 ml/min.

The results were as follows:

| Sorbitol (Molarity in Eluate) | Cryo (Purity over Plasma) | Recovery (%) | Final Purity (over Plasma) |
|---|---|---|---|
| 0 | 60× | 42 | 2600× |
| 0 | 60× | 55 | 2000× |
| 0 | 60× | 35 | 1800× |
| 0 | 60× | 31 | 1810× |
| 1 | 60× | 71 | 3870× |
| 1 | 60× | 85 | 4100× |
| 1 | 60× | 72 | 2700× |
| 1 | 60× | 71 | 3500× |

The above results indicate that use of maleic anhydride polyelectrolyte resin is a viable alternative to use of aminohexyl sepharose.

The results of aminohexyl sepharose chromatography have not always been as favorable as reported above. The present inventors have associated this with variations in the quality of batches of the sepharose.

The present invention is particularly appropriate for purification of constituents and products of genetically engineered micro-organisms.

Although specific embodiments of the invention have been disclosed for illustrative purposes, it will be appreciated by those skilled in the art that many additions, substitutions, and modifications are possible without departing from the scope and spirit of the invention. For example, although the AHF protein is described herein, the present purification method may be applied to all proteins that are stabilized and/or preferentially hydrated by sugars, alcohols, amino acids or salts.

The present invention is most suitable for purification of proteins that are present either in small quantitites in biological fluids or that are desired to be recovered at a high yield. Such proteins include but are not limited to other coagulation factors, such as II, VII, IX, and X. Albumin and immunoglobulin may also be purified by this method, although only when high recovery is important, as it is believed that the present method would not be cost-effective for albumin or immunoglobulin purification under normal circumstances (i.e. when it is necessary to purify relatively large amounts of a protein and less complete recovery can be tolerated). For each protein, the optimum concentration of each hydration additive for chromatography would have to be determined. This can be done by the methods discussed above.

We claim:

1. In a process for purifying a protein that has antihemophilic factor activity by column chromatography in a column behaving predominantly as an ion-exchange chromatography column comprising the stages of:
   (a) equilibrating said chromatography column;
   (b) loading a sample containing said protein on said column, causing said protein to adsorb onto said column;
   (c) washing said column;
   (d) eluting said adsorbed protein from said column by causing it to desorb from said column; and
   (e) recovering said protein in purified form; the improvement comprising the step of:
      adding to the column a substance consisting essentially of an effective amount for selectively increasing the electrostatic forces on the surface of said protein and concomitantly decreasing the hydrophobicity of said protein of a hydration additive selected from the group consisting of sugars and polyhydric alcohols during at least one of said stages (a), (b), and (c) thereby promoting the adsorption of said protein on said column.

2. The process of claim 1 wherein said hydration additive is a sugar selected from the group consisting of sucrose, maltose, lactose, glucose, ribose, arabinose, galactose, fructose, mannose, rhamnose, raffinose, melezitose, dextran, xylose, allose, 6-deoxymannose, and 6-deoxygalactose.

3. The process of claim 1 wherein said hydration additive is a polyhydric alcohol selected from the group consisting of sorbitol, mannitol, inositol, adonitol, erythritol, ethylene glycol, glycerol, propylene glycol, xylitol, 2-methyl-2,4-pentanediol, ficoll and ribitol.

4. The process of claim 1 wherein said chromatography column is an ion exchange chromatography column.

5. The process of claim 4 wherein said chromatography is anion exchange chromatography.

6. The process of claim 4 wherein said additive is incorporated into a buffer used to load said sample onto said column.

7. The process of claim 6 wherein said additive is eliminated from said column prior to elution of said protein.

8. A process according to claim 2 wherein said additive is selected from the group consisting of sucrose, maltose, lactose, glucose, sorbitol and mannitol.

9. A process according to claim 8 wherein said additive is sucrose and its concentration ranges between about 0.5 and 2.0M.

10. A process according to claim 8 wherein said additive is maltose and its concentration ranges between about 0.2 and 0.4M.

11. A process according to claim 8 wherein said additive is glucose and its concentration ranges between about 0.5 and 2.0M.

12. A process according to claim 8 wherein said additive is sorbitol and its concentration ranges between about 0.5 and 2.0M.

13. A process according to claim 6 wherein said additive is also incorporated into a buffer used to equilibrate said column.

14. A process according to claim 13 wherein said column chromatography employs as a chromatographic medium a quaternary aminoethyl anion exchange resin.

15. The process of claim 13 wherein the eluting step involves use of a physiologically acceptable detergent to enhance desorption of said protein from the column.

16. The process of claim 15 wherein said additive is sorbitol used at a concentration ranging between about 0.5 and 2.0M.

17. The process of claim 16 wherein said detergent is polysorbate 80 at a concentration ranging between about 0.01 and 0.1%.

18. The process of claim 17 wherein said sorbitol concentration is about 1M.

19. The process of claim 1 further comprising using as said sample in said stage (a) an eluate containing said protein from a hydrophobic affinity column chromatography.

20. The process of claim 1 said process further comprising subjecting said eluate containing said protein from said stage (d) to a second purification using a second column behaving predominantly as a hydrophobic affinity chromatography column.

21. The process of claim 1 wherein said column is a mixed ion exchange/hydrophobic affinity chromatography column behaving predominantly as an ion exchange chromatography column.

22. The process of claim 21 wherein said column is a maleic anhydride polyelectrolyte column.

23. The process of claim 20 said second purification comprising the stages of:
   (i) equilibrating said second chromatography column;
   (ii) loading said stage (d) eluate containing said protein on said column causing said protein to absorb to said second column;
   (iii) washing said second column; and
   (iv) eluting said adsorbed protein from said second column by causing it to desorb from said second column, adding to the column during said stage (iv) a substance consisting essentially of an effective amount for selectively increasing the electrostatic forces on the surface of said protein and concomitantly decreasing the hydrophobicity of said protein of a hydration additive consisting of sugars and polyhydric alcohols, thereby promoting the desorption of said protein from said second column.

24. The process of claim 23 wherein said additive is selected from the group consisting of sucrose, maltose, lactose, glucose, sorbitol and mannitol.

* * * * *